United States Patent
Grubisic (10) Patent No.: US 11,834,656 B2
(45) Date of Patent: Dec. 5, 2023

(54) CLOSED LOOP CONTINUOUS APTAMER DEVELOPMENT SYSTEM

(71) Applicant: X Development LLC, Mountain View, CA (US)

(72) Inventor: Ivan Grubisic, Oakland, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 17/126,842

(22) Filed: Dec. 18, 2020

(65) Prior Publication Data

US 2021/0189385 A1 Jun. 24, 2021

Related U.S. Application Data

(60) Provisional application No. 62/952,875, filed on Dec. 23, 2019.

(51) Int. Cl.
*C12N 15/10* (2006.01)
*C12N 15/115* (2010.01)
*G16B 35/20* (2019.01)

(52) U.S. Cl.
CPC ........ *C12N 15/1089* (2013.01); *C12N 15/115* (2013.01); *G16B 35/20* (2019.02); *C12N 2310/16* (2013.01); *C12N 2310/3231* (2013.01)

(58) Field of Classification Search
None
See application file for complete search history.

(56) References Cited

PUBLICATIONS

International Application No. PCT/US2020/065954, International Preliminary Report on Patentability, dated Jul. 7, 2022, 17 pages.
Eremeeva et al., "Highly Stable Hexitol Based XNA Aptamers Targeting the Vascular Endothelial Growth Factor", Nucleic Acids Research, 2019, vol. 47, Issue 10, Apr. 10, 2019, pp. 4927-4939.
International Application No. PCT/US2020/065954, "Invitation to Pay Additional Fees and, Where Applicable, Protest Fee", Apr. 28, 2021, 4 pages.
Rangel et al., "In Vitro Selection of an Xna Aptamer Capable of Small-Molecule Recognition", Nucleic Acids Research, vol. 46, Issue 16, Jul. 31, 2018, pp. 8057-8068.
Taylor et al., "Selecting Fully-Modified XNA Aptamers Using Synthetic Genetics", Current Protocols In Chemical Biology, vol. 10, Issue 2, May 18, 2018, 23 pages.
Wang et al., "Three Decades of Nucleic Acid Aptamer Technologies: Lessons Learned, Progress And Opportunities on Aptamer Development", Biotechnology Advance, vol. 37, Issue 1, Jan. 1, 2019, 23 pages.
Knight et al., "Array-Based Evolution of DNA Aptamers Allows Modelling of an Explicit Sequence-Fitness Landscape", Nucleic Acids Research, vol. 37, Issue 1, 2009, 10 pages.
International Application No. PCT/US2020/065954, International Search Report and Written Opinion, dated Aug. 3, 2021, 22 pages.
Sabri et al., "In-Silico Selection of Aptamer: A Review on the Revolutionary Approach to Understand the Aptamer Design and Interaction Through Computational Chemistry", Materials Today: Proceedings, vol. 19, Issue 4, 2019, pp. 1572-1581.
Zhou et al., "Searching the Sequence Space for Potent Aptamers Using SELEX in Silico", Journal of Chemical Theory and Computation, vol. 11, Issue 12, Dec. 2015, 8 pages.
Japanese Application No. JP2022-536529, "Office Action", dated Aug. 9, 2023, 11 pages.

*Primary Examiner* — Sean McGarry
(74) *Attorney, Agent, or Firm* — Kilpatrick Townsend & Stockton LLP (57) ABSTRACT

The present disclosure relates to a closed loop aptamer development system that identifies one or more aptamers observed experimentally and implements machine-learning models to identify other aptamers not observed experimentally. Particularly, aspects of the present disclosure are directed to receiving a query concerning one or more targets, acquiring a library of aptamers that potential satisfy the query, identifying a first set of aptamers from the library of aptamers that substantially or completely satisfy the query, obtaining sequence data for the first set of aptamers, generating, by a prediction model, a third set of aptamers derived from the sequence data for the first set of aptamers, validating the third set of aptamers that substantially or completely satisfy the query, and upon validating the third set of aptamers and in response to the query, providing the third set of aptamers as a result to the query.

8 Claims, 6 Drawing Sheets

CLOSED LOOP CONTINUOUS APTAMER DEVELOPMENT SYSTEM

CROSS-REFERENCES TO RELATED APPLICATIONS

The present application is a non-provisional application of, and claims the benefit and priority under 35 U.S.C. 119(e) of U.S. Provisional Application No. 62/952,875, filed Dec. 23, 2019, the entirety of which is hereby incorporated herein by reference in its entirety for all purposes.

FIELD

The present disclosure relates to development of aptamers, and in particular to a closed loop aptamer development system that identifies one or more aptamers observed experimentally and implements machine-learning models to identify other aptamers not observed experimentally.

BACKGROUND

Aptamers are short sequences of single-stranded oligonucleotides (e.g., anything that is characterized as a nucleic acid, including xenobases). The sugar backbone of the single-stranded oligonucleotides functions as the acid and the A, T, C, G refers to the base. An aptamer can involve modifications to either the acid or the base. Aptamers have been shown to selectively bind to specific targets (e.g., proteins, protein complexes, peptides, carbohydrates, inorganic molecules, organic molecules such as metabolites, cells, etc.) with high binding affinity. Further, aptamers can be highly specific, in that a given aptamer may exhibit high binding affinity for one target but low binding affinity for many other targets. Thus, aptamers can be used to (for example) bind to disease-signature targets to facilitate a diagnostic process, bind to a treatment target to effectively deliver a treatment, bind to target molecules within a mixture to facilitate purification, etc. However, the utility of an aptamer hinges on a degree to which it effectively binds to a target.

Frequently, an iterative experimental process (e.g., Systematic Evolution of Ligands by EXponential Enrichment (SELEX)) is used to identify aptamers that are selectively bound to target molecules with high affinity. In the iterative experimental process, a nucleic acid library of oligonucleotide strands (aptamers) is incubated with a target molecule. Then, the target-bound oligonucleotide strands are separated from the unbound strands and amplified via polymerase chain reaction (PCR) to seed a new pool of oligonucleotide strands. This selection process is continued for a number (e.g., 6-15) rounds with increasingly stringent conditions, which ensure that the oligonucleotide strands obtained have the highest affinity to the target molecule.

The nucleic acid library typically includes $10^{14}$-$10^{15}$ random oligonucleotide strands (aptamers). However, there are approximately a septillion ($10^{24}$) different aptamers that could be considered. Exploring this full space of candidate aptamers is impractical. However, given that present-day experiments are now only a sliver of the full space, it is highly likely that optimal aptamer selection is not currently being achieved. This is particularly true when it is important to assess the degree to which aptamers bind with multiple different targets, as a fewer portion of aptamers will have the desired combination of binding affinities across the targets. Accordingly, while substantive studies on aptamers have progressed since the introduction of the SELEX process, it would take an enormous amount of resources and time to experimentally evaluate a septillion ($10^{24}$) different aptamers every time a new target is proposed. In particular, there is a need for improving upon current experimental limitations with scalable machine-learning modeling techniques to identify aptamers and derivatives thereof that selectively bind to target molecules with high affinity.

SUMMARY

In various embodiments, a method is provided that includes synthesizing an XNA aptamer library from one or more single stranded DNA or RNA (ssDNA or ssRNA) libraries; partitioning a plurality of aptamers within the XNA aptamer library into monoclonal compartments that combined establish a compartment-based capture system, where each monoclonal compartment comprises a unique aptamer from the plurality of aptamers; capturing, by the compartment-based capture system, one or more targets, where the capturing comprises the one or more targets binding to the unique aptamer within one or more monoclonal compartments; separating the one or more monoclonal compartments of the compartment-based capture system that comprise the one or more targets bound to the unique aptamer from a remainder of monoclonal compartments of the compartment-based capture system that do not comprise the one or more targets bound to a unique aptamer; sequencing the unique aptamer from each of the one or more monoclonal compartments, where the sequencing comprises generating sequencing data and analysis data for the unique aptamer from each of the one or more monoclonal compartments; and generating, by a prediction model, one or more aptamer sequences derived from the sequencing data and the analysis data for at least some of the unique aptamers from the one or more monoclonal compartments.

In some embodiments, the method further includes synthesizing another XNA aptamer library from the one or more aptamer sequences derived from the sequencing data and the analysis data; partitioning a plurality of derived aptamers within the another XNA aptamer library into monoclonal compartments that combined establish another compartment-based capture system, where each monoclonal compartment comprises a unique derived aptamer from the plurality of derived aptamers; capturing, by the another compartment-based capture system, the one or more targets, where the capturing comprises the one or more targets binding to the unique derived aptamer sequence within one or more monoclonal compartments; separating the one or more monoclonal compartments of the another compartment-based capture system that comprise the one or more targets bound to the unique derived aptamer from a remainder of monoclonal compartments of the another compartment-based capture system that do not comprise the one or more targets bound to a unique derived aptamer; and in response to the separating, validating the unique derived aptamer from each of the one or more monoclonal compartments as an aptamer having a high binding affinity with the one or more targets.

In some embodiments, the method further includes eluting the unique aptamer from each of the one or more monoclonal compartments; and amplifying the unique aptamer from each of the one or more monoclonal compartments by enzymatic or chemical processes, where the one or more monoclonal compartments are one or more monoclonal beads.

In some embodiments, the analysis data for the unique aptamer from each of the one or more monoclonal compartments indicates the unique aptamer did bind to the one or more targets.

In some embodiments, the sequencing further comprises generating count data for the unique aptamer from each of the one or more monoclonal compartments, and the one or more aptamer sequences are generated as being derived from the sequencing data, the analysis data, and the count data for at least some of the unique aptamers from the one or more monoclonal compartments.

In some embodiments, the method further includes recording the one or more aptamer sequences derived from the sequencing data and the analysis data in a data structure in association with the one or more targets.

In some embodiments, the method further includes predicting, by another prediction model, a count or analysis of the one or more aptamer sequences derived from the sequencing data and the analysis data for at least some of the unique aptamers from the one or more monoclonal compartment; and recording the one or more aptamer sequences derived from the sequencing data and the analysis data in a data structure in association with the one or more targets and the predicted count or analysis of the one or more aptamer sequences.

In some embodiments, the one or more monoclonal compartments are separated from the remainder of monoclonal compartments using a fluorescence-activated cell sorting system.

In various embodiments, a computer-implemented method is provided that includes: receiving a query concerning one or more targets; acquiring a library of aptamers that potential satisfy the query; identifying a first set of aptamers from the library of aptamers that substantially or completely satisfy the query and a second set of aptamers from the library of aptamers that does not substantially or completely satisfy the query; obtaining sequence data for the first set of aptamers; generating, by a prediction model, a third set of aptamers derived from the sequence data for the first set of aptamers; validating the third set of aptamers that substantially or completely satisfy the query; and upon validating the third set of aptamers and in response to the query, providing the third set of aptamers as a result to the query.

In some embodiments, the providing the result to the query further comprising providing the third set of aptamers and the first set of aptamers as the result to the query.

In some embodiments, the computer-implements method further includes obtaining sequence data for the second set of aptamers, where the third set of aptamers is generated as being derived from the sequence data for first set of aptamers and the sequence data for the second set of aptamers.

In some embodiments, the computer-implements method further includes recording the third set of aptamers in a data structure in association with the one or more targets.

In some embodiments, the computer-implements method further includes obtaining analysis data for the first set of aptamers, and where the third set of aptamers are generated as being derived from the sequence data for first set of aptamers and the analysis data.

In some embodiments, the computer-implements method further includes: predicting, by another prediction model, an analysis for each aptamer of the third set of aptamers derived from the sequence data for first set of aptamers and the analysis data for the first set of aptamers; and recording the third set of aptamers in a data structure in association with the one or more targets and the predicted analysis for each aptamer of the third set of aptamers.

In some embodiments, the analysis data for the first set of aptamers includes a binary classifier or a multiclass classifier selected based on the query, and the predicted analysis for the third set of aptamers includes the binary classifier or the multiclass classifier.

In some embodiments, (i) the binary classifier indicates that each aptamer from the first set of aptamers functionally inhibited the one or more targets, functionally did not inhibit the one or more targets, bound to the one or more targets, or did not bound to the one or more targets, or (ii) the multiclass classifier indicates a level of functional inhibition or a gradient scale for binding affinity with respect to each aptamer from the first set of aptamers and the one or more targets.

In some embodiments, the computer-implements method further includes obtaining count data for the first set of aptamers, where the count data for the first set of aptamers indicates a count of each aptamer within the first set of aptamers, and where the third set of aptamers are generated as being derived from the first set of aptamers and the count data.

In some embodiments, the computer-implements method further includes: predicting, by another prediction model, a count for each aptamer of the third set of aptamers derived from the sequence data for the first set of aptamers and the count data for the first set of aptamers; and recording the third set of aptamers in a data structure in association with the one or more targets and the predicted count for each aptamer of the third set of aptamers.

In some embodiments, a system is provided that includes one or more data processors and a non-transitory computer readable storage medium containing instructions which, when executed on the one or more data processors, cause the one or more data processors to perform part or all of one or more methods or processes disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be better understood in view of the following non-limiting figures, in which.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. Introduction

Systematic evolution of ligands by exponential enrichment (SELEX) is a powerful in vitro selection process conventionally used to identify oligonucleotide sequences (aptamers) with desired properties (usually high affinity for a target) from randomized nucleic acid libraries. To date, thousands of aptamers targeting amino acids, proteins, small metal ion, organic molecules, bacteria, viruses, whole cells and animals have been developed using one form or another of the SELEX. These aptamers have been widely applied in analytical, bioanalytical, imaging, diagnostic and therapeutic fields. Despite great achievements, there still exists a larger lag in the successful clinical use of therapeutic aptamers than that of therapeutic antibodies. Currently, there are a number of barriers attributed to the impediment of aptamer development and application. First, the SELEX process is still time consuming, and the successful rates are low (each phase of the cycle can be labor-intensive, resource and time consuming, and require special expertise). Second, most of the current aptamers are obtained in vitro, and whether they can function in vivo needs to be elucidated. Third, the main method to identify the individual sequence of the final enriched library has been using classic Sanger sequencing analysis. In most cases, the final library contains thousands of sequences, for which it is hard to identify which one is the best aptamer. In addition, the most abundant sequences of the final selection round are not always the ones with the highest affinity and specificity.

To address these limitations and problems, a closed loop system is disclosed herein for developing aptamers. For instance in an exemplary embodiment, the development of the aptamers may include synthesizing an XNA aptamer library from one or more single stranded DNA or RNA (ssDNA or ssRNA) libraries, partitioning a plurality of aptamers within the XNA aptamer library into monoclonal compartments that combined establish a compartment-based capture system, where each monoclonal compartment comprises a unique aptamer from the plurality of aptamers, capturing, by the compartment-based capture system, one or more targets, where the capturing comprises the one or more targets binding to the unique aptamer within one or more monoclonal compartments, separating the one or more monoclonal compartments of the compartment-based capture system that comprise the one or more targets bound to the unique aptamer from a remainder of monoclonal compartments of the compartment-based capture system that do not comprise the one or more targets bound to a unique aptamer, sequencing the unique aptamer from each of the one or more monoclonal compartments, where the sequencing comprises generating sequencing data and analysis data for the unique aptamer from each of the one or more monoclonal compartments, and generating, by a prediction model, one or more aptamer sequences derived from the sequencing data and the analysis data for at least some of the unique aptamers from the one or more monoclonal compartments.

To further address these limitations and problems, a closed loop system is disclosed herein for identifying aptamers as a solution for a query. For example, a query may be received concerning one or more particular targets and in silico derived oligonucleotide sequences (aptamers) may be identified that best satisfy the query. The in silico oligonucleotide sequences may be derived using machine-learning techniques from the in vitro or experimentally derived oligonucleotide sequences. The identified in silico derived oligonucleotide sequences may then be validated in vitro or experimentally to assess binding affinities with the one or more particular targets. In one exemplary embodiment, a computer-implemented method is provided that comprises. In an exemplary embodiment, the identification of the aptamers as a solution for a query may include receiving a query concerning one or more targets, acquiring a library of aptamers that potential satisfy the query, identifying a first set of aptamers from the library of aptamers that substantially or completely satisfy the query and a second set of aptamers from the library of aptamers that does not substantially or completely satisfy the query, obtaining sequence data for the first set of aptamers, generating, by a prediction model, a third set of aptamers derived from the sequence data for the first set of aptamers, validating the third set of aptamers that substantially or completely satisfy the query, and upon validating the third set of aptamers and in response to the query, providing the third set of aptamers as a result to the query.

It will be appreciated that techniques disclosed herein can be applied to assess other biological material rather than aptamers. For example, alternatively or additionally, the techniques described herein may be used to assess the interaction between any type of biologic material (e.g., a whole or part of an organism such as *E. coli*, or a biologic product that is produced from living organisms, contain components of living organisms, or derived from human, animal, or microorganisms by using biotechnology) with one or more objects.

II. Aptamer Development Techniques

Figure 1A:
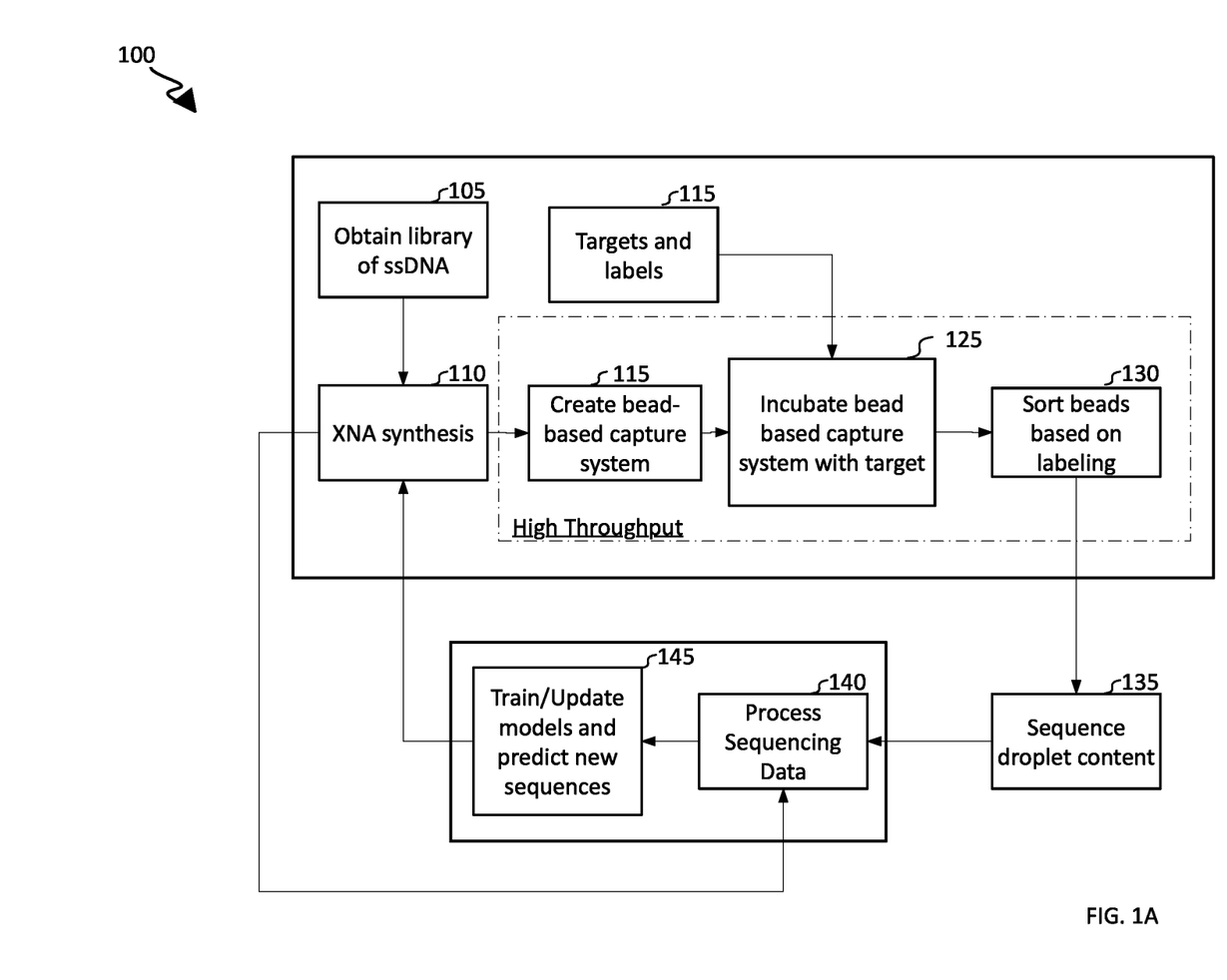
FIGS. 1A and 1B show block diagrams of a aptamer development platform according to various embodiments.

FIG. 1A shows a block diagram of an aptamer development platform 100 for strategically identifying particular aptamers for experiments to assess queries such as binding affinities or product inhibition with respect to one or more particular targets. In various embodiments, the aptamer development platform 100 implements screening-based techniques for aptamer discovery where each aptamer candidate sequence in a library is assessed based on the query (e.g., binding affinity with one or more targets or functionally capable of inhibiting one or more targets) in a high-throughput manner. In some embodiments, the aptamer development platform 100 implements machine learning based techniques for enhanced aptamer discovery where each aptamer candidate sequence in a library that satisfies the query is input into one or more machine-learning models to predict additional aptamer candidate sequences that potentially satisfy the query. In some embodiments, the aptamer development platform 100 further implements screening-based techniques for aptamer validation to validate or confirm that the predicted additional aptamer candidate sequences do satisfy the query (e.g., bind or inhibit the one or more targets). As should be understood, these techniques from screening through prediction to validation can be repeated in one or more closed loop processes sequentially or in parallel to ultimately assess any number of queries in a high through-put manner.

The aptamer development platform 100 includes obtaining one or more single stranded DNA or RNA (ssDNA or ssRNA) libraries at block 105. The one or more single stranded DNA or RNA (ssDNA or ssRNA) libraries may be obtained from a third party (e.g., an outside vendor) or may be synthesized in-house, and each of the one or more libraries typically contains up to $10^{17}$ different unique sequences. At block 110, the ssDNA or ssRNA of the one or more libraries are transcribed to synthesize a Xeno nucleic acid (XNA) aptamer library. XNA aptamer sequences such as threose nucleic acids (TNA) are synthetic nucleic acid analogues that have a different sugar backbone than the natural nucleic acids DNA and RNA. XNA may be selected for the aptamer sequences as these polymers are not readily recognized and degraded by nucleases, and thus are well-suited for in vivo applications. XNA aptamer sequences may be synthesized in vitro through enzymatic or chemical synthesis. For example, a XNA library of aptamers may be generated by primer extension of some or all of the oligonucleotide strands in a ssDNA library, flanking the aptamer sequences with fixed primer annealing sites for enzymatic amplification, and subsequent PCR amplification to create an XNA aptamer library that includes $10^{12}$-$10^{17}$ aptamer sequences.

In some instances, the XNA aptamer library may be processed for application in downstream machine-learning processes. In certain instances, the aptamer sequences are processed for use as training data, test data, or validation data in one or more machine-learning models. In other instances, the aptamer sequences are processed for use as actual experimental data in one or more trained machine-learning models. In either instance, the aptamer sequences may be processed to generate initial sequence data comprising a representation of the sequence of each aptamer and optionally a count metric. The representation of the sequence can include one-hot encoding of each nucleotide in the sequence that maintains information about the order of the nucleotides in the aptamer. The representation of the sequence can additionally or alternatively include a string of category identifiers, with each category representing a particular nucleotide. The count metric can include a count of each aptamer in the XNA aptamer library.

At block 115, the aptamers within the XNA aptamer library are partitioned into monoclonal compartments (e.g., monoclonal beads or compartmentalized droplets) for high-throughput aptamer selection. For example, the aptamers may be attached to beads to generate a bead-based capture system for a target. Each bead may be attached to a unique aptamer sequence generating a library of monoclonal beads. The library of monoclonal beads may be generated by sequence-specific partitioning and covalent attachment of the sequences to the beads, which may be polystyrene or glass beads. In some instances, the sequence-specific partitioning includes hybridization of XNA aptamers with capture oligonucleotides having an amine modified nucleotide for interaction with covalent attachment chemistries coated on the surface of a bead. In certain instances, the covalent attachment chemistries include N-hydroxysuccinimide (NETS) modified PEG, cyanuric chloride, isothiocyanate, nitrophenyl chloroformate, hydrazine, or any combination thereof.

At block 120, a target (e.g., proteins, protein complexes, peptides, carbohydrates, inorganic molecules, cells, etc.) is obtained. The target may be obtained as a result of query posed by a user (e.g., a client or customer). For example, a user may pose a query concerning identification of ten aptamers with the highest binding affinity for a given target or twenty aptamers with the greatest ability to inhibit activity of a given target. In some instances, the target is tagged with a label such as a fluorescent probe. At block 125, the bead-based capture system is incubated with the labeled target to allow for the aptamers to bind with the target and form aptamer-target complexes.

At block 130, the beads having aptamer-target complexes are separated from the beads having non-binding aptamers using a separation protocol. In some instances, the separation protocol includes a fluorescence-activated cell sorting system (FACS) to separate the beads having the aptamer-target complexes from the beads having non-binding aptamers. For example, a suspension of the bead-based capture system may be entrained in the center of a narrow, rapidly flowing stream of liquid. The flow may be arranged so that there is separation between beads relative to their diameter. A vibrating mechanism causes the stream of beads to break into individual droplets (e.g., one bead per droplet). Before the stream breaks into droplets, the flow passes through a fluorescence measuring station where the fluorescent label which is part of the aptamer-target complexes is measured. An electrical charging ring may be placed at a point where the stream breaks into droplets. A charge may be placed on the ring based on the prior fluorescence measurement, and the opposite charge is trapped on the droplet as it breaks from the stream. The charged droplets may then fall through an electrostatic deflection system that diverts droplets into containers based upon their charge (e.g., droplets having beads with aptamer-target complexes go into one container and droplets having beads with non-binding aptamers go into a different container). In some instances, the charge is applied directly to the stream, and the droplet breaking off retains a charge of the same sign as the stream. The stream may then returned to neutral after the droplet breaks off.

At block 135, the aptamers from the aptamer-target complexes are eluted from the beads and target, and amplified by enzymatic or chemical processes to optionally prepare for subsequent rounds of selection (repeat blocks 110-130, for example a SELEX protocol). The stringency of the elution conditions can be increased to identify the tightest-binding or highest affinity sequences. In some instances, once the aptamers are separated and amplified, the aptamers may be sequenced to identify the sequence and optionally a count for each aptamer. Optionally, the beads having non-binding aptamers are eluted from the beads, and amplified by enzymatic or chemical processes. In some instances, once the non-binding aptamers are separated and amplified, the non-binding aptamers may be sequenced to identify the sequence and optionally a count for each non-binding aptamer.

At block 140, the sequence, the count, and an analysis performed based on the separation protocol (e.g., a binary classifier or a multiclass classifier) for each aptamer that has gone through the selection process of steps 110-130 are processed for application in downstream machine-learning processes. Each aptamer may include only the binding aptamers (those that formed the aptamer-target complexes), only the non-binding aptamers (those that did not form the aptamer-target complexes), or the combination thereof. In general, there are different types of binders (e.g., agonist, antagonist, allosteric, etc.) and those would be characteristics that the system may be configured to distinguish between the different types of binders during training, testing, and/or experimental analysis. In some instances, the sequence, count, and analysis for each aptamer is processed for use as training data, test data, or validation data in one or more machine-learning models. In other instances, the sequence, count, and analysis for each aptamer is processed for use as actual experimental data in one or more trained machine-learning models. In either instance, the sequence, count, and analysis for each aptamer may be processed to generate selection sequence data comprising a representation of the sequence of each aptamer, a count metric, an analysis metric, or any combination thereof. The representation of the sequence can include one-hot encoding of each nucleotide in the sequence that maintains information about the order of the nucleotides in the aptamer. The representation of the sequence can additionally or alternatively include other features concerning the sequence and/or aptamer, for example, post-translational modifications, binding sites, enzyme active sites, local secondary structure, kmers or characteristics identified for specific kmers, etc. The representation of the sequence can additionally or alternatively include a string of category identifiers, with each category representing a particular nucleotide. The count metric may include a count of the aptamer detected subsequent to an exposure to the target (e.g., during incubation and potentially in the presence of other aptamers). In some instances, the count metric includes a count of the aptamer detected subsequent to an exposure to the target in each round of selection. The analysis metric may include a binary classifier such as functionally inhibited the target, functionally did not inhibit the target, bound to the target, or did not bound to the target, a multiclass classifier such as a level of functional inhibition or a gradient scale for binding affinity.

At block 145, one or more machine-learning models are trained using the initial sequence data (from block 110), the selection sequence data (from block 135), or a combination thereof. The one or more machine-learning models may include a neural network, such as a feedforward neural network, recurrent neural network, convolutional neural network, and/or a deep neural network. The machine-learning models may be trained using training data, test data, and validation data based on sets of initial sequence data and selection sequence data to predict sequences for derived aptamers (e.g., aptamers not experimentally determined by a selection process but predicted based on aptamers experimentally determined by a selection process) and optional counts and/or analytics for the predicted sequences for derived aptamers. A loss function, such as an Mean Square Error (MSE), likelihood loss, or log loss (cross entropy loss), may be used to train each of the one or more machine-learning models. In some instances, a machine-learning model may be trained for predicting sequences for derived aptamers using the initial sequence data and/or the selection sequence data. Another machine-learning model may be trained for predicting binding counts for the predicted sequences for derived aptamers using the initial sequence data and/or the selection sequence data. Another machine-learning model may be trained for predicting analytics such as binding affinity for the predicted sequences for derived aptamers using the initial sequence data and/or the selection sequence data.

The trained machine-learning models can then be used to predict sequences for derived aptamers and optional counts and/or analytics for the predicted sequences for derived aptamers. For example, a subset of the aptamers experimentally determined by the selection process to satisfy the query (e.g., aptamers that have high binding affinity with a target or predicted counts due primarily to high binding affinity with a target) can be identified and separated from aptamers experimentally determined by the selection process to not satisfy the query. The subset of the aptamers experimentally determined by the selection process to satisfy the query can then be input into one or more machine learning models to identify in silico derived aptamer sequences (e.g., aptamer sequences that are derivatives of the experimentally selected aptamers) and optionally counts and analytics for the derived aptamer sequences. Optionally, the subset of the aptamers experimentally determined by the selection process to not satisfy the query can also be input into one or more machine learning models to assist in identifying in silico derived aptamer sequences (e.g., aptamer sequences that are derivatives of the experimentally selected aptamers) and optionally counts and analytics for the derived aptamer sequences.

The output can trigger experimental testing of some or all of the in silico derived aptamer sequences to experimentally measure analytics such as binding affinities with the target and/or binding affinities with one or more other targets. The experimental testing may be conditioned on input from a user. For example, a user device may present an interface in which the in silico derived aptamer sequences are identified along with input components configured to receive input to modify the in silico derived aptamer sequences (e.g., by removing or adding aptamers) and/or to generate an experiment-instruction communication to be sent to another device and/or other system. The experiment can include producing each of the in silico derived aptamer sequences. These aptamers can then be validated in the wet lab in either individual or bulk experiments. For example, the user can access a single aptamer (e.g. oligonucleotide). The single aptamer can be provided by an aptamer source, such as Twist Biosciences, Agilent, IDT, etc. The aptamer can be used to conduct biochemical assays (e.g. gel shift, surface plasma resonance, bio-layer interferometry, etc.). In some instances, multiple aptamers in a singular pool can be used to rerun the equivalent SELEX protocol (e.g., blocks 115-140) to identify enriched aptamers. Results can be assessed to determine whether the computational experiments are verified. In some instances, selections can be run in a digital format (i.e., ones that gave a functional output per sequence) to validate particular sequences. The validated sequences can be used to update the training set because the pair of sequence and affinity metric can be both normalized and calibrated.

Figure 1B:
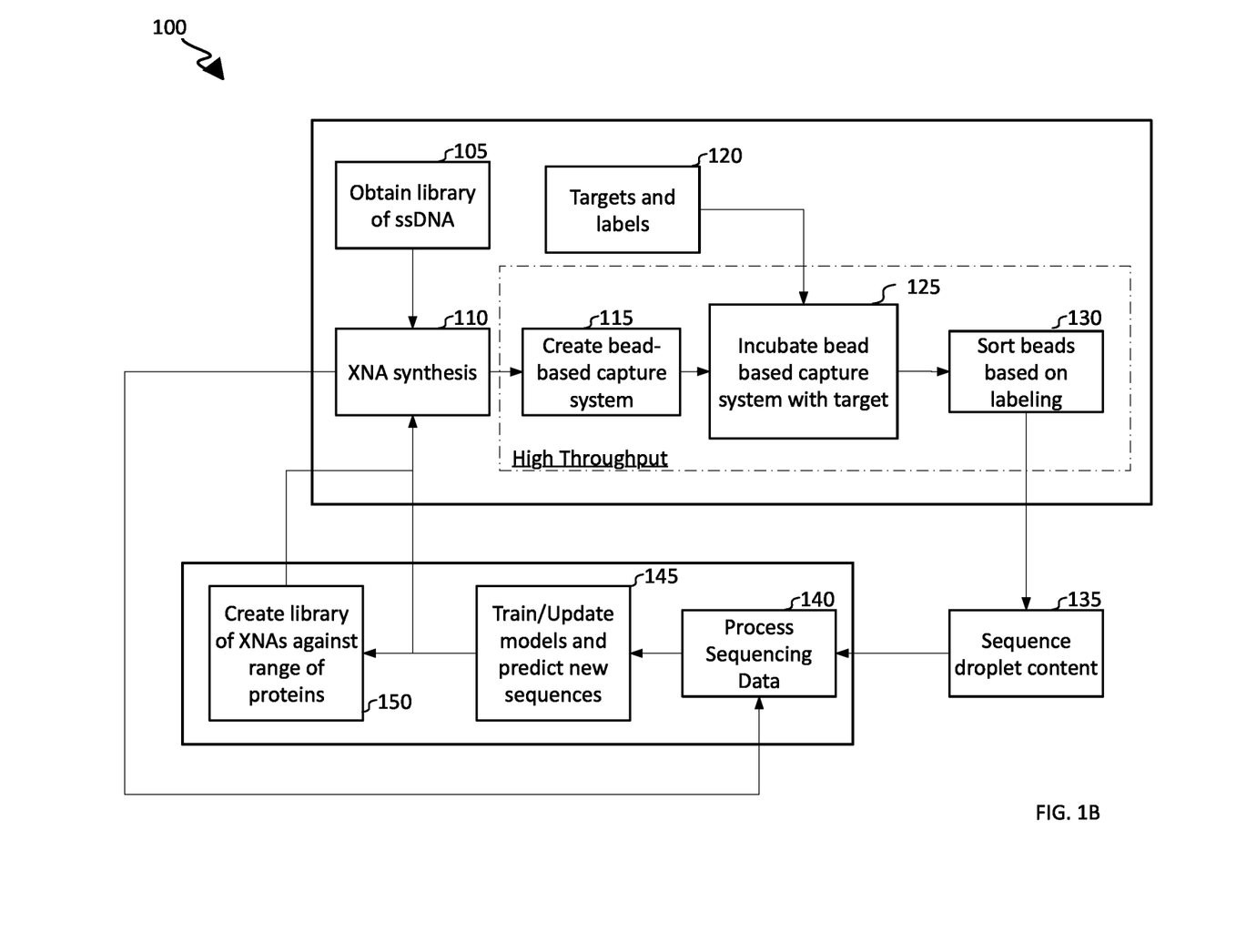

FIG. 1B shows a block diagram of an alternative aptamer development platform 100 for strategically identifying particular aptamers for experiments to assess queries such as binding affinities or product inhibition with respect to one or more particular targets. In various embodiments, the aptamer development platform 100 implements screening-based techniques for aptamer discovery where each aptamer candidate sequence in a library is assessed based on the query (e.g., binding affinity with one or more targets or functionally capable of inhibiting one or more targets) in a high-throughput manner, as described with respect to FIG. 1A. Additionally, the aptamer development platform 100 may implement machine learning based techniques for enhanced aptamer discovery where a library of predicted sequences for derived aptamers against a range of queries and/or targets is generated for subsequent processing (e.g., used as a base library of aptamer sequences in experimental testing (steps 110-140), instead of a random pool of oligonucleotides or aptamers, to answer a new query).

More specifically, at step 150, the output of the trained machine-learning models (sequences for derived aptamers and optional counts and/or analytics of the predicted sequences for derived aptamers) can trigger recording of some or all of the in silico derived aptamer sequences (e.g., positive and negative aptamer data such as predicted counts demonstrating increased binding affinity for a target or predicted counts demonstrating decreased binding affinity for a target) within a data structure (e.g., a database table). In some instances, the sequences for the derived aptamers are recorded in the data structure in association with additional information including the query, the one or more targets that are the focus of the query and basis for the genesis of the sequences for the derived aptamers, counts predicted for the sequences for the derived aptamers, analysis predicted for the sequences for the derived aptamers, or any combination thereof.

As should be understood, the aptamer development platform 100 described with respect to FIGS. 1A and 1B could be used for aptamer discovery where steps 110-140 are run in parallel to generate multiple monoclonal beads against multiple targets in association with one or more queries. Additionally or alternatively, the aptamer development platform 100 described with respect to FIGS. 1A and 1B could be used for aptamer discovery where steps 110-145 are run in parallel to generate multiple monoclonal beads against multiple targets in association with one or more queries and predict in parallel sequences for derived aptamers and optional counts and/or analytics for the predicted sequences for derived aptamers. The machine-learning models trained and used to make the predictions may be updated with results from the experiments and other machine-learning models using a distributed or collaborative learning approach such as federate learning which trains machine-learning models using decentralized data residing on end devices or systems. For example, a central or primary model may be updated or trained with results from all experiments being run and the results of the updating/training of the central or primary model may be propagated through to deployed secondary models (e.g., if information is obtained on cytokine a then the system may use that information to potential refine processes to identify for cytokine b).

III. Modeling Techniques to Predict Sequences for Derived Aptamers

Figure 2:
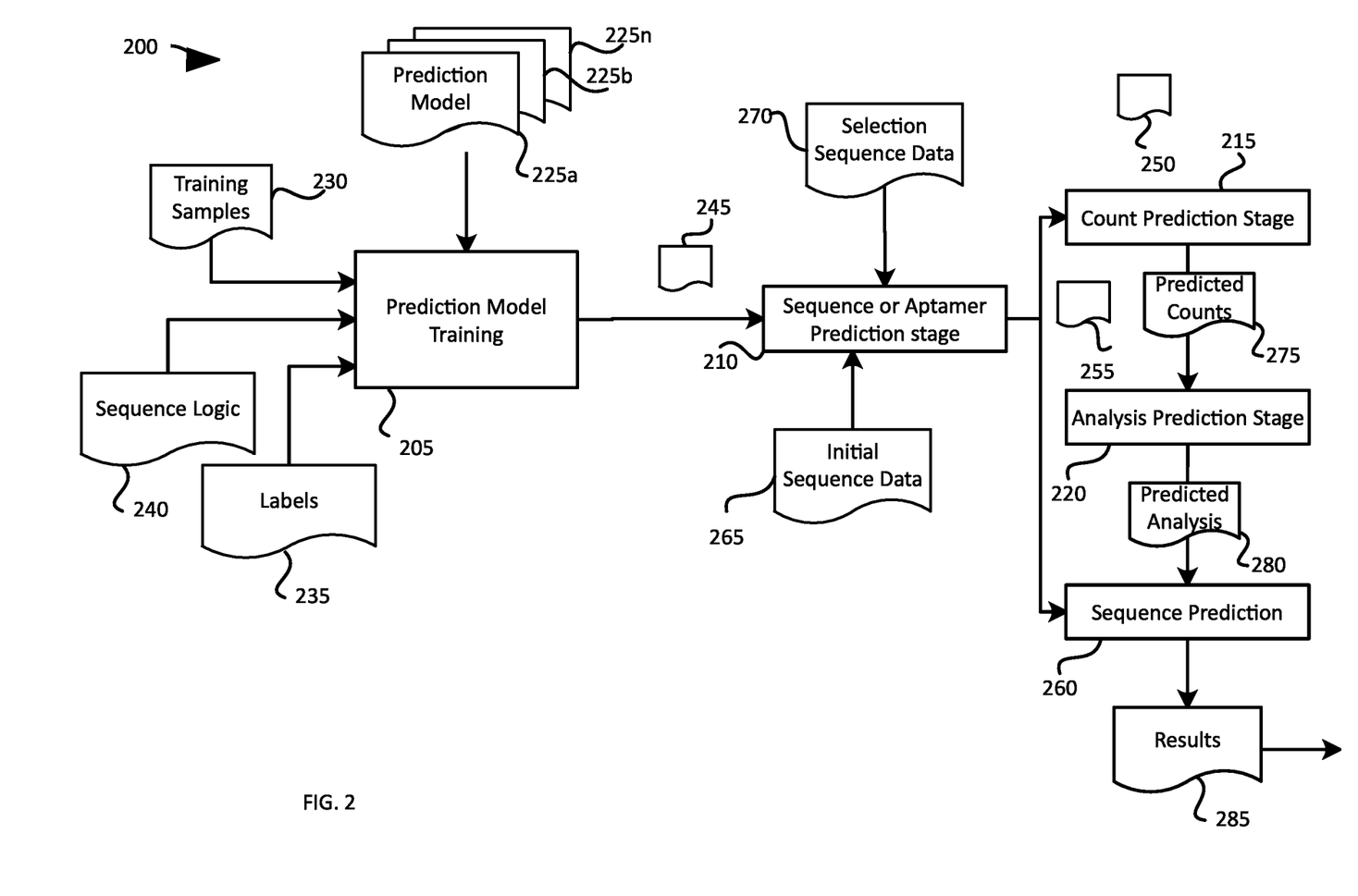
FIG. 2 shows a machine-learning modeling system for developing aptamers in accordance with various embodiments.

FIG. 2 shows a block diagram illustrating aspects of a machine-learning modeling system 200 for predicting sequences for derived aptamers (e.g., aptamers that answer a query posed by a user). As shown in FIG. 2, the predictions performed by the machine-learning modeling system 200 in this example include several stages: a prediction model training stage 205, a sequence or aptamer prediction stage 210, a count prediction stage 215, and an analysis prediction stage 220. The prediction model training stage 205 builds and trains one or more prediction models 225a-225n ('n' represents any natural number) to be used by the other stages (which may be referred to herein individually as a prediction model 225 or collectively as the prediction models 225). For example, the prediction models 225 can include a model for predicting sequences or aptamers not experimentally determined by a selection process but predicted based on aptamers experimentally determined by a selection process. The prediction models 230 can also include a model for predicting binding counts for the predicted sequences for derived aptamers. The prediction models 230 can also include a model for predicting analytics such as binding affinity for the predicted sequences for derived aptamers. Still other types of prediction models may be implemented in other examples according to this disclosure.

A prediction model 225 can be a machine-learning model, such as a neural network, a convolutional neural network ("CNN"), e.g. an inception neural network, a residual neural network ("Resnet") or NASNET provided by GOOGLE LLC from MOUNTAIN VIEW, CALIFORNIA, or a recurrent neural network, e.g., long short-term memory ("LSTM") models or gated recurrent units ("GRUs") models. A prediction model 225 can also be any other suitable machine-learning model trained to predict latent variables, sequence counts or aptamer sequences from experimentally determined aptamer sequences, such as a support vector machine, decision tree, a three-dimensional CNN ("3DCNN"), a dynamic time warping ("DTW") technique, a hidden Markov model ("HMI"), etc., or combinations of one or more of such techniques—e.g., CNN-HMM or MCNN (Multi-Scale Convolutional Neural Network). In various instances, at least one of the prediction models 225a-n includes structures related to a loss function prior to training. The machine-learning modeling system 200 may employ the same type of prediction model or different types of prediction models for aptamer sequence prediction, aptamer count prediction, and analysis prediction.

To train the various prediction models 225 in this example, training samples 230 for each prediction model 225 are obtained or generated. The training samples 230 for a specific prediction model 225 can include the initial sequence data and the selection sequence data as described with respect to FIG. 1 and optional labels 235 corresponding to the initial sequence data and the selection sequence data. For example, for a prediction model 225 to be utilized to predict derived aptamer sequences based on a given sequence, the input can be the aptamer sequence itself or features extracted from the selection sequence data associated with the aptamer sequence and optional labels 235 can include known derivative sequences. Similarly, for a prediction model 225 to be utilized to predict a count or binding affinity for an aptamer sequence, the input can include the sequence and count features extracted from the initial sequence data and/or the selection sequence data associated with the sequence, and the optional labels 235 can include features indicating parameters for the count or binding affinity or a vector indicating probabilities for the count or binding affinity of the selection sequence data.

In some instances, the training process includes iterative operations to find a set of parameters for the prediction model 225 that minimizes a loss function for the prediction models 225. Each iteration can involve finding a set of parameters for the prediction model 225 so that the value of the loss function using the set of parameters is smaller than the value of the loss function using another set of parameters in a previous iteration. The loss function can be constructed to measure the difference between the outputs predicted using the prediction models 225 and the optional labels 235 contained in the training samples 230. Once the set of parameters are identified, the prediction model 225 has been trained and can be tested, validated, and/or utilized for prediction as designed.

In addition to the training samples 225, other auxiliary information can also be employed to refine the training process of the prediction models 225. For example, sequence logic 240 can be incorporated into the prediction model training stage 205 to ensure that the sequences or aptamers, counts, and analysis predicted by a prediction model 225 do not violate the sequence logic 240. For example, binding affinity (the strength of the binding interaction between an aptamer and a target) is a characteristic that can drive aptamers to be present in greater numbers in a pool of aptamer-target complexes after a cycle of selection process. This relationship can be expressed in the sequence logic 240 such that as the binding affinity variable increases the predictive count increases (to represent this characteristic), as the binding affinity variable decreases the predictive count decreases. Moreover, an aptamer sequence generally has inherent logic among the different nucleotides. For example, GC content for an aptamer is typically not greater than 60%. This inherent logical relationship between GC content and aptamer sequences can be exploited to facilitate the aptamer sequence prediction.

According to some aspects of the disclosure presented herein, the logical relationship between the binding affinity and count can be formulated as one or more constraints to the optimization problem for training the prediction models 225. A training loss function that penalizes the violation of the constraints can be built so that the training can take into account the binding affinity and count constraints. Alternatively, or additionally, structures, such as a directed graph, that describe the current features and the temporal dependencies of the prediction output can be used to adjust or refine the features and predictions of the prediction models 225. In an example implementation, features may be extracted from the initial sequence data and combined with features from the selection sequence data as indicated in the directed graph. Features generated in this way can inherently incorporate the temporal, and thus the logical, relationship between the initial library and subsequent pools of aptamer sequences after cycles of the selection process. Accordingly, the prediction models 225 trained using these features can capture the logical relationships between sequence characteristics, selection cycles, aptamer sequences, and nucleotides.

Although the training mechanisms described herein mainly focus on training a prediction model 225, these training mechanisms can also be utilized to fine tune existing prediction models 225 trained from other datasets. For example, in some cases, a prediction model 225 might have been pre-trained using pre-existing aptamer sequence libraries. In those cases, the prediction models 225 can be retrained using the training samples 225 containing initial sequence data, experimentally derived selection sequence data, and other auxiliary information as discussed herein.

The prediction model training stage 205 outputs trained prediction models 225 including the trained sequence prediction models 245, trained count prediction models 250, and trained analysis prediction models 255. The trained sequence prediction models 245 may be used in the sequence prediction stage 210 to generate sequence predictions 260 for a subset or all of the initial sequence data 265 and/or the selection sequence data 270 identified during the experimental selection process (e.g., steps 110-140 described with respect to FIGS. 1A and 1B). The trained count prediction models 250 may be used in the count prediction stage 215 to generate count predictions 275 for the predicted sequences based on the initial sequence data 265 and/or the selection sequence data 270 identified during the experimental selection process (e.g., steps 110-140 described with respect to FIGS. 1A and 1B). The trained analysis prediction models 255 may be used in the analysis prediction stage 220 to generate analysis predictions 280 (e.g., a binary classifier such as binds to target or does not bind to target) for the predicted sequences based on the initial sequence data 265 and/or the selection sequence data 270 identified during the experimental selection process (e.g., steps 110-140 described with respect to FIGS. 1A and 1B). In some instances, a results stage 285 may use the sequence predictions 260, count predictions 275, analysis predictions 280, or any combination thereof to provide results to a query posed by a user. For example, the results stage 285, in response to query for top ten aptamers that bind a given target, may provide the sequence predictions for ten aptamers with the highest count or binding affinity for the given target.

Figure 3:
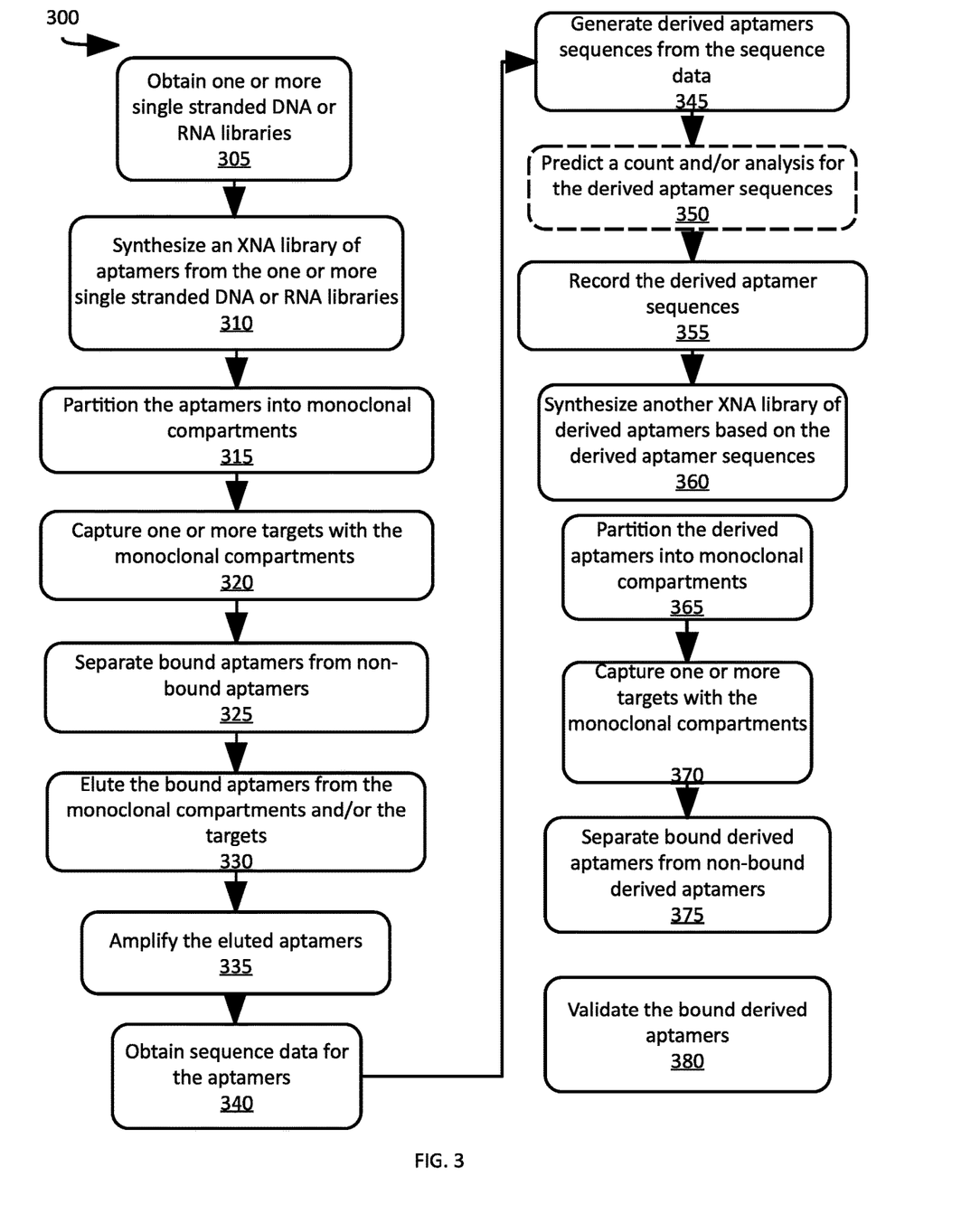
FIG. 3 shows an exemplary flow for aptamer development in accordance with various embodiments.

FIG. 3 is a simplified flow chart 300 illustrating an example of processing for developing aptamers using an aptamer development platform and a machine-learning modeling system and technique (e.g., the aptamer development platform 100 and machine-learning modeling system and technique 200 described with respect to FIGS. 1A, 1B, and 2). Process 300 begins at block 305, at which one or more single stranded DNA or RNA (ssDNA or ssRNA) libraries are obtained. The one or more ssDNA or ssRNA libraries comprise a plurality of ssDNA or ssRNA sequences. At block 310, synthesizing an XNA aptamer library from the one or more ssDNA or ssRNA libraries. The XNA aptamer sequences that make up the XNA aptamer library may be synthesized in vitro with a transcription assay that includes enzymatic or chemical synthesis. The XNA aptamer library comprises a plurality of aptamer sequences. At block 315, the plurality of aptamers within the XNA aptamer library are partitioned into monoclonal compartments that combined establish a compartment-based capture system. Each monoclonal compartment comprises a unique aptamer from the plurality of aptamers. In some instances, the one or more monoclonal compartments are one or more monoclonal beads.

At block 320, the compartment-based capture system is used to capture one or more targets. The capturing comprises the one or more targets binding to the unique aptamer within one or more monoclonal compartments. In some instances, the one or more targets are identified based on a query received from a user. As used herein, when an action is "based on" something, this means the action is based at least in part on at least a part of the something. At block 325, the one or more monoclonal compartments of the compartment-based capture system that comprise the one or more targets bound to the unique aptamer are separated from a remainder of monoclonal compartments of the compartment-based capture system that do not comprise the one or more targets bound to a unique aptamer. In some instances, the one or more monoclonal compartments are separated from the remainder of monoclonal compartments using a fluorescence-activated cell sorting system. At block 330, the unique aptamer is eluted from each of the one or more monoclonal compartments and/or the one or more targets. At block 335, the unique aptamer from each of the one or more monoclonal compartments is amplified by enzymatic or chemical processes. At block 340, the unique aptamer from each of the one or more monoclonal compartments (e.g., the bound aptamers) are sequenced. The sequencing comprises using a sequencer to generate sequencing data and optionally analysis data for the unique aptamer from each of the one or more monoclonal compartments. The analysis data for the unique aptamer from each of the one or more monoclonal compartments may indicate the unique aptamer did bind to the one or more targets. In some instances, the sequencing further comprises generating count data for the unique aptamer from each of the one or more monoclonal compartments. In some instances, the sequencing further comprises sequences of unique aptamers from the remainder of the monoclonal compartments (e.g., non-bound aptamers). The sequencing further comprises using a sequencer to generate sequencing data and optionally analysis data for the unique aptamer from each of the remainder of the monoclonal compartments.

At block 345, one or more aptamer sequences are generated by a prediction model as being derived from the sequencing data and optionally the analysis data for at least some of the unique aptamers from the one or more monoclonal compartments. In some instances, the one or more aptamer sequences are generated as being derived from the sequencing data and optionally the analysis data and/or the count data for at least some of the unique aptamers from the one or more monoclonal compartments. Additionally, the one or more aptamer sequences may be generated as being derived from the sequencing data and optionally the analysis data for at least some of the unique aptamers from the remainder of the monoclonal compartments. Optionally at block 350, a count or analysis of the one or more aptamer sequences is predicted by another prediction model as being derived from the sequencing data and optionally the analysis data and/or count data for at least some of the unique aptamers from the one or more monoclonal compartment and/or at least some of the unique aptamers from the remainder of the monoclonal compartments. At block 355, the generated one or more aptamer sequences and optionally the predicted analysis data and/or count data are recorded in a data structure in association with the one or more targets.

At block 360, another XNA aptamer library is synthesized from the one or more aptamer sequences derived from the sequencing data and optionally the analysis data. At block 365, a plurality of derived aptamers within the another XNA aptamer library are partitioned into monoclonal compartments that combined establish another compartment-based capture system. Each monoclonal compartment comprises a unique derived aptamer from the plurality of derived aptamers. At block 370, another compartment-based capture system is used to capture the one or more targets. The capturing comprises the one or more targets binding to the unique derived aptamer sequence within one or more monoclonal compartments. At block 375, the one or more monoclonal compartments of the another compartment-based capture system that comprise the one or more targets bound to the unique derived aptamer are separated from a remainder of monoclonal compartments of the another compartment-based capture system that does not comprise the one or more targets bound to a unique derived aptamer. At block 380, in response to the separating, the unique derived aptamer from each of the one or more monoclonal compartments is validated as an aptamer having a high binding affinity with the one or more targets. As used herein, "binding affinity" is a measure of the strength of attraction between an aptamer and a target. As used herein, a "high binding affinity" is a result from stronger intermolecular forces between an aptamer and a target leading to a longer residence time at the binding site (higher "on" rate, lower "off" rate).

Figure 4:
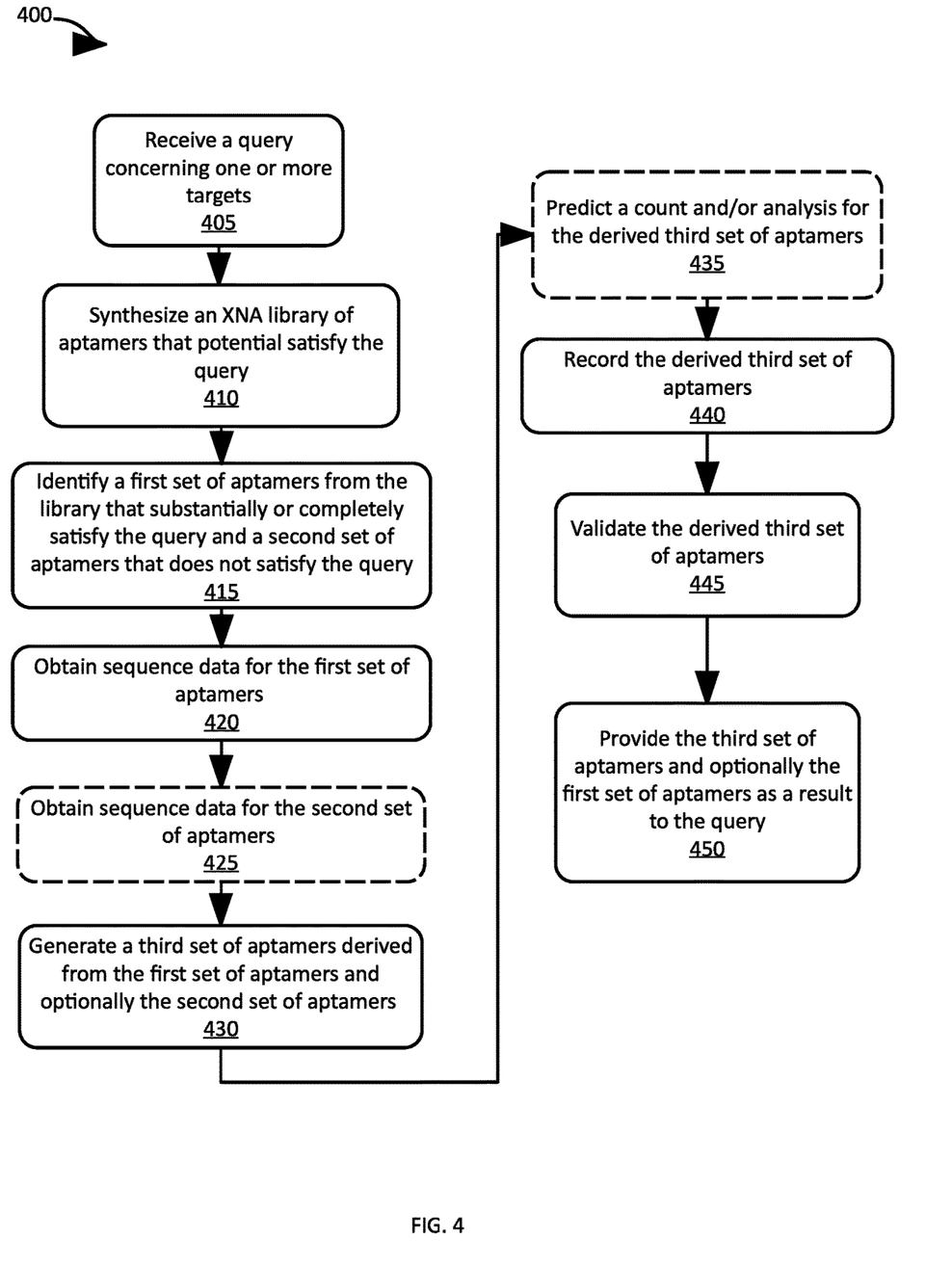
FIG. 4 shows an exemplary flow for providing results to a query in accordance with various embodiments.

FIG. 4 is a simplified flow chart 400 illustrating an example of processing for providing results to a query using an aptamer development platform and a machine-learning modeling system and technique (e.g., the aptamer development platform 100 and machine-learning modeling system and technique 200 described with respect to FIGS. 1A, 1B, and 2). Process 400 begins at block 405, at which a query is received concerning one or more targets. For example, a user may pose a query concerning identification of ten aptamers with the highest binding affinity for a given target or twenty aptamers with the greatest ability to inhibit activity of a given target. At block 410, a library of aptamers that potential satisfy the query is obtained. At block 415, a first set of aptamers from the library of aptamers is identified that substantially or completely satisfy the query and a second set of aptamers from the library of aptamers that does not substantially or completely satisfy the query. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

At block 420, sequence data for the first set of aptamers is obtained. Optionally, analysis data and/or count data are also obtained for the first set of aptamers. In some instances, the analysis data for the first set of aptamers includes a binary classifier or a multiclass classifier selected based on the query. The binary classifier may indicate that each aptamer from the first set of aptamers functionally inhibited the one or more targets, functionally did not inhibit the one or more targets, bound to the one or more targets, or did not bound to the one or more targets; whereas the multiclass classifier may indicate a level of functional inhibition or a gradient scale for binding affinity with respect to each aptamer from the first set of aptamers and the one or more targets. At optional block 425, sequence data is obtained for the second set of aptamers.

At block 430, a third set of aptamers is generated by a prediction model as being derived from the sequence data for the first set of aptamers and optionally the analysis data for the first set of aptamers, the count data for the first set of aptamers, the second set of aptamers, or any combination thereof. At optional block 435, an analysis for each aptamer of the third set of aptamers is predicted by another prediction model as being derived from the sequence data for first set of aptamers and the analysis data for the first set of aptamers. In some instances, the predicted analysis for the third set of aptamers includes the binary classifier or the multiclass classifier. At optional block 435, a count for each aptamer of the third set of aptamers is predicted by another prediction model as being derived from the sequence data for first set of aptamers and the count data for the first set of aptamers. At block 440, the third set of aptamers and optionally the predicted analysis and/or count for each aptamer of the third set of aptamers are recorded in a data structure in association with the one or more targets. At block 445, the third set of aptamers are validated as substantially or completely satisfying the query. At block 450, upon validating the third set of aptamers and in response to the query, the third set of aptamers is provided as a result to the query. In some instances, the providing the result to the query further comprises providing the third set of aptamers and the first set of aptamers as the result to the query.

Figure 5:
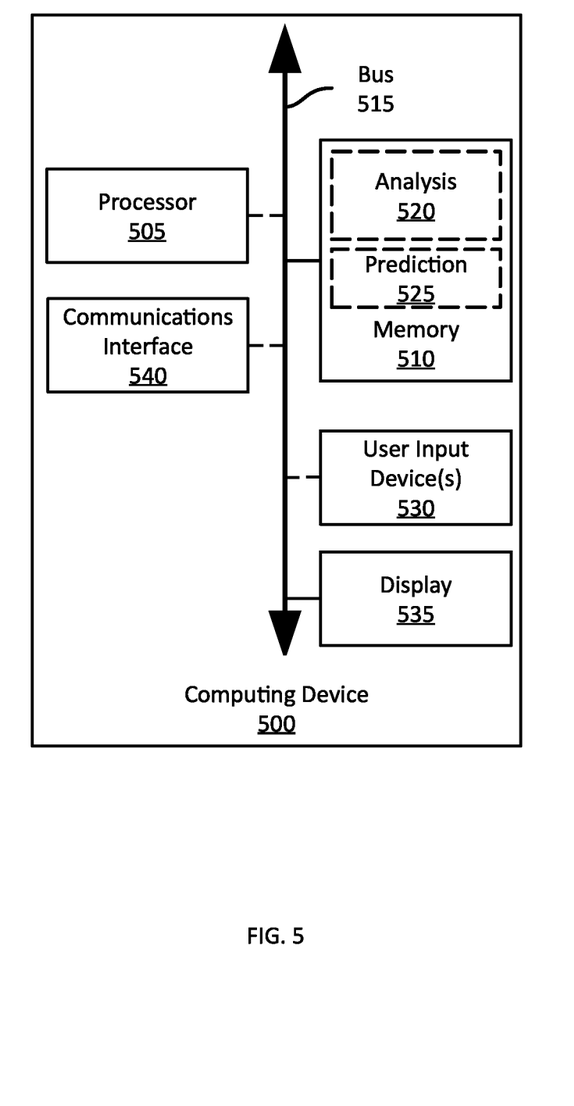
FIG. 5 shows an exemplary computing device in accordance with various embodiments.

FIG. 5 illustrates an example computing device 500 suitable for use with systems and methods for developing aptamers or providing results to a query according to this disclosure. The example computing device 500 includes a processor 505 which is in communication with the memory 510 and other components of the computing device 500 using one or more communications buses 515. The processor 505 is configured to execute processor-executable instructions stored in the memory 510 to perform one or more methods for developing aptamers or providing results to a query according to different examples, such as part of all of the example method 300 or 400 described above with respect to FIGS. 4 and 5. In this example, the memory 510 stores processor-executable instructions that provide sequence data analysis 520 and aptamer sequence prediction 525, as discussed above with respect to FIGS. 1A, 1B 2, 3, and 4.

The computing device 500, in this example, also includes one or more user input devices 530, such as a keyboard, mouse, touchscreen, microphone, etc., to accept user input. The computing device 500 also includes a display 535 to provide visual output to a user such as a user interface. The computing device 500 also includes a communications interface 540. In some examples, the communications interface 540 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

IV. Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method comprising:
synthesizing an XNA aptamer library from one or more single stranded DNA or RNA (ssDNA or ssRNA) libraries;
partitioning a plurality of aptamers within the XNA aptamer library into monoclonal compartments that combined establish a compartment-based capture system, wherein each monoclonal compartment comprises a unique aptamer from the plurality of aptamers;
capturing, by the compartment-based capture system, one or more targets, wherein the capturing comprises the one or more targets binding to the unique aptamer within one or more monoclonal compartments;
separating the one or more monoclonal compartments of the compartment-based capture system that comprise the one or more targets bound to the unique aptamer from a remainder of monoclonal compartments of the compartment-based capture system that do not comprise the one or more targets bound to a unique aptamer;
sequencing the unique aptamer from each of the one or more monoclonal compartments, wherein the sequencing comprises generating sequencing data and analysis data for the unique aptamer from each of the one or more monoclonal compartments;
generating selection sequence data for at least some of the unique aptamers from the one or more monoclonal compartments based on the sequencing data and the analysis data associated with each of the unique aptamers, wherein the selection sequence data comprises a representation of the sequence of each of the unique aptamers and an analysis metric of each of the unique aptamers; inputting the selection sequence data into a machine learning model; and
predicting, by the machine learning model, one or more aptamer sequences derived from the selection sequence data, wherein the one or more aptamer sequences are predicted based on the sequencing data and the analysis data for the at least some of the unique aptamers from the one or more monoclonal compartments.

2. The method of claim 1, further comprising:
synthesizing another XNA aptamer library from the one or more aptamer sequences derived from the selection sequence data;
partitioning a plurality of derived aptamers within the another XNA aptamer library into monoclonal compartments that combined establish another compartment-based capture system, wherein each monoclonal compartment comprises a unique derived aptamer from the plurality of derived aptamers;
capturing, by the another compartment-based capture system, the one or more targets, wherein the capturing comprises the one or more targets binding to the unique derived aptamer sequence within one or more monoclonal compartments;
separating the one or more monoclonal compartments of the another compartment-based capture system that comprise the one or more targets bound to the unique derived aptamer from a remainder of monoclonal compartments of the another compartment-based capture system that do not comprise the one or more targets bound to a unique derived aptamer; and
in response to the separating, validating the unique derived aptamer from each of the one or more monoclonal compartments as an aptamer having a high binding affinity with the one or more targets.

3. The method of claim 1, further comprising:
eluting the unique aptamer from each of the one or more monoclonal compartments; and
amplifying the unique aptamer from each of the one or more monoclonal compartments by enzymatic or chemical processes,
wherein the one or more monoclonal compartments are one or more monoclonal beads.

4. The method of claim 1, wherein the analysis data for the unique aptamer from each of the one or more monoclonal compartments comprises binding information that indicates the unique aptamer did bind to the one or more targets, the analysis metric includes a binary classifier that indicates the unique aptamer did bind to the one or more targets, and the representation of the sequence of each of the unique aptamers includes an encoding of each nucleotide in the sequence that maintains information about an order of the nucleotides in the unique aptamer.

5. The method of claim 1, wherein the sequencing further comprises generating count data for the unique aptamer from each of the one or more monoclonal compartments, the selection sequence data is generated for at least some of the unique aptamers from the one or more monoclonal compartments based on the sequencing data, the count data, and the analysis data associated with each of the unique aptamers, wherein the selection sequence data comprises the representation of the sequence of each of the unique aptamers, a count metric of each of the unique aptamers, and the analysis metric of each of the unique aptamers, the count metric is a count of the unique aptamer detected subsequent to the capturing, and the one or more aptamer sequences are predicted based on the sequencing data, the analysis data, and the count data for the at least some of the unique aptamers from the one or more monoclonal compartments.

6. The method of claim 1, further comprising recording the one or more aptamer sequences derived from the selection sequence data in a data structure in association with the one or more targets.

7. The method of claim 1, further comprising:
predicting, by another machine learning model, a count or analysis of the one or more aptamer sequences derived from the selection sequence data; and
recording the one or more aptamer sequences derived from the selection sequence data in a data structure in association with the one or more targets and the predicted count or analysis of the one or more aptamer sequences.

8. The method of claim 7, further comprising receiving a query concerning the one or more targets, and generating, using the data structure, a response to the query based on the one or more aptamer sequences and the predicted count or analysis of the one or more aptamer sequences.

\* \* \* \* \*